US008828552B2

United States Patent
Neumann et al.

(10) Patent No.: US 8,828,552 B2
(45) Date of Patent: Sep. 9, 2014

(54) METHOD FOR PRODUCING AN ANTI-INFECTIVE COATING ON IMPLANTS

(75) Inventors: Hans-Georg Neumann, Rostock (DE); Cornelia Prinz, Marlow (DE)

(73) Assignee: Dot GmbH, Rostock (DE)

(*) Notice: Subject to any disclaimer, the term of this patent is extended or adjusted under 35 U.S.C. 154(b) by 192 days.

(21) Appl. No.: 13/130,431

(22) PCT Filed: Jan. 4, 2010

(86) PCT No.: PCT/EP2010/050010
§ 371 (c)(1),
(2), (4) Date: Aug. 2, 2011

(87) PCT Pub. No.: WO2010/076338
PCT Pub. Date: Jul. 8, 2010

(65) Prior Publication Data
US 2012/0024712 A1      Feb. 2, 2012

(30) Foreign Application Priority Data
Jan. 5, 2009   (EP) .................................. 09100006

(51) Int. Cl.
*C25D 5/02*   (2006.01)
*A61L 27/54*   (2006.01)
*A61L 27/06*   (2006.01)
*A61L 27/30*   (2006.01)

(52) U.S. Cl.
CPC ................ *A61L 27/06* (2013.01); *A61L 27/54* (2013.01); *A61L 2300/404* (2013.01); *A61L 2300/104* (2013.01); *A61L 27/306* (2013.01); *A61L 2300/102* (2013.01)
USPC ......... 428/472.1; 205/122; 205/171; 205/173

(58) Field of Classification Search
None
See application file for complete search history.

(56) References Cited

U.S. PATENT DOCUMENTS

| 5,833,463 | A | 11/1998 | Hurson | |
| 8,414,908 | B2* | 4/2013 | Jin et al. | 424/423 |
| 2002/0099449 | A1 | 7/2002 | Speitling | |
| 2005/0060021 | A1 | 3/2005 | O'Brien et al. | |
| 2006/0161256 | A1* | 7/2006 | Ziegler et al. | 623/11.11 |

(Continued)

FOREIGN PATENT DOCUMENTS

| DE | 20020649 | 4/2002 |
| DE | 10241137 | 3/2004 |

(Continued)

OTHER PUBLICATIONS

Oh et al. Biomaterials, 26, 2005, p. 4938-4943.*

(Continued)

*Primary Examiner* — Vera Katz
(74) *Attorney, Agent, or Firm* — McNees Wallace & Nurick LLC

(57) ABSTRACT

The invention relates to a method for producing an anti-infective coating on implants that contain titanium or are composed of titanium. The aim of the invention is to provide a coating method with which it is possible, for implants made of titanium or that contain titanium, to combine the optimization of the mechanical properties achieved with the anodic oxidation type II with the optimization of the anti-infective properties. According to the invention, the implants are anodically oxidized in an alkaline solution, then metal having anti-infective properties is electrodeposited on said surface, and afterwards the oxide layer containing metal is solidified.

8 Claims, 1 Drawing Sheet

(56) References Cited

U.S. PATENT DOCUMENTS

| | | | |
|---|---|---|---|
| 2006/0229715 A1* | 10/2006 | Istephanous et al. | 623/1.46 |
| 2008/0306554 A1* | 12/2008 | McKinley | 606/301 |
| 2009/0220561 A1* | 9/2009 | Jin et al. | 424/423 |

FOREIGN PATENT DOCUMENTS

| | | |
|---|---|---|
| DE | 10243132 | 4/2004 |
| JP | H06125979 A | 5/1994 |
| JP | H08289927 A | 11/1996 |
| JP | 2005287985 A | 10/2005 |
| WO | WO2006116752 A2 * | 11/2006 |
| WO | 2007144667 A2 | 12/2007 |
| WO | 2008091835 A2 | 7/2008 |

OTHER PUBLICATIONS

Sul et al. Journal of Materials Science:Materials in Medicine, 12, 2001, p. 1025-1031.*

* cited by examiner

METHOD FOR PRODUCING AN ANTI-INFECTIVE COATING ON IMPLANTS

BACKGROUND OF THE INVENTION

The invention relates to a method for producing an anti-infective coating on implants, that contain titanium or are composed of titanium.

From DE 10243132 B4 is known to provide implants made of titanium or titanium alloys with a titanium oxide coating, in which metal ions such as silver and copper are homogeneously distributed, by using a sol-gel method. For the mechanical stabilization and densification of said coating a heat treatment is applied after drying. By means of heating to about 500° C. a ceramization of the coating takes place. For the implants the heat treatment has the disadvantage that it results in a loss of strength. Therefore, it is not suitable for implants which must have high fatigue strength.

It is known that an anodic oxidation type II of titanium results in a greater hardness and higher fatigue strength. In DE 20020649 U1 this coating is also described as an anti-infective coating because of its smooth surface, besides silver and copper. However, it is not possible to produce a sufficiently adherent coating of silver or copper on an anodic oxidation type II coating.

SUMMARY OF THE INVENTION

The invention is based on the object to provide a coating method by means of which it is possible for implants made of titanium or which contain titanium to combine the optimization of the mechanical properties achieved by the anodic oxidation type II with the optimization of the anti-infective properties.

This object is solved in that the implants are oxidized anodically in an alkaline solution, then metal having anti-infective properties is electrodeposited on the surface, and afterwards the metal-containing oxide layer is solidified. The electrolyte for the anodic oxidation may contain an aqueous solution of, for example, sodium hydroxide or sodium silicate (water glass).

In the anodic oxidation a conversion layer containing oxygen and optionally other atoms, and a porous titanium oxide layer having a sufficient conductivity, which is electrically conductive in the pores, such that metal can be electrodeposited in it, can be formed. By blasting, e.g. with glass beads, the metal-containing oxide layer is solidified, and more weakly bound oxide and metal particles are removed or more intensely connected with each other and with the surface of the implant.

There is provided a method for the combined modification of implants containing titanium or consisting of titanium, wherein in the first step a porous oxide layer is formed by anodic spark discharge in strongly alkaline electrolytes, in the second step the galvanic charge of metal into the porous layer takes place, and in a third step the metal-enriched oxide layer is solidified by blasting and can be more or less eliminated by removing more weakly bound oxide or metal particles or by connecting said particles more intensely with each other and the implant.

The elution of the metal starting under physiological conditions may be adjusted in regard to its concentration by variation of the mean metal coating of the implant surface, so that an antimicrobial or rather antibacterial action without any substantial damage to the cells of the surrounding body tissue is achieved. In particular copper, silver and zinc are suitable as metals. In the case of the metal copper there can be additionally expected an improved blood flow of the newly formed body tissue due to the catalytic effect on the angiogenesis. The thickness of the metal-containing layer is advantageously 8-15 μm, preferably 10 μm. Solidifying the metal-containing oxide layer is advantageously carried out by blasting with glass beads.

DETAILED DESCRIPTION OF THE INVENTION

In the following the invention is explained in more detail by way of an example.

Example 1

Coating

Figure 1:
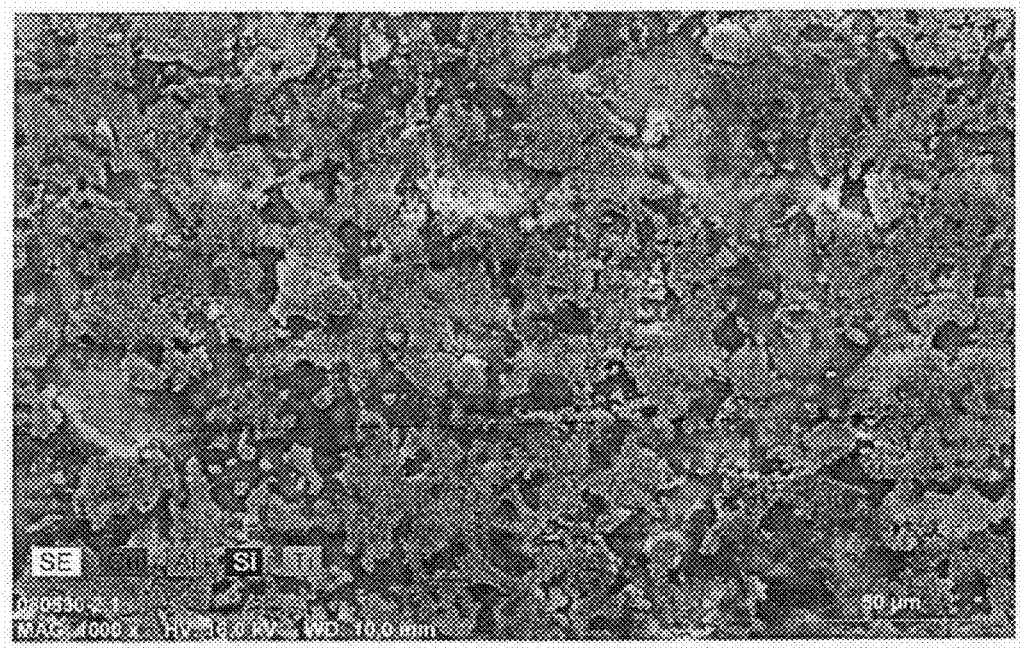
FIG. 1 is a microphotograph of a copper-coated TiAlV-surface.

TiAl6V4-samples are coated with a porous oxide layer according to the principle of anodic spark discharge in a strongly alkaline electrolyte. For that, 50 g NaOH are dissolved in 500 ml of distilled water. In the solution heated to 40° C., the anodic spark oxidation of the titanium sample is conducted by slowly increasing the voltage to 40 volt. Then, copper from a saturated copper acetate solution is added into the porous oxide layer by means of cathode deposition. The resulting copperenriched oxide layer is partially removed by glass bead blasting, and the copper contained in it is almost completely incorporated in an island-like manner into the sample surface (FIG. 1).

Example 2

Description of the Antibacterial Mechanism

For testing the antibacterial action investigations were performed on clinically relevant bacterial strain staphylococcus aureus ATCC25923. For that, TiAlV-cylinders with a diameter of 8 mm and a length of 20 mm were coated with copper according to Example 1, and situated for various times in 6 ml of a PBS buffer solution at 37° C. which had been vaccinated with 150 μl of bacterial suspension. Thereafter, the concentration of the living bacteria on the cylinders and in the solution was determined by plating on agar culture media and by situating (48 h) the cylinders in buffer solution at 30° C.

Figure 2:
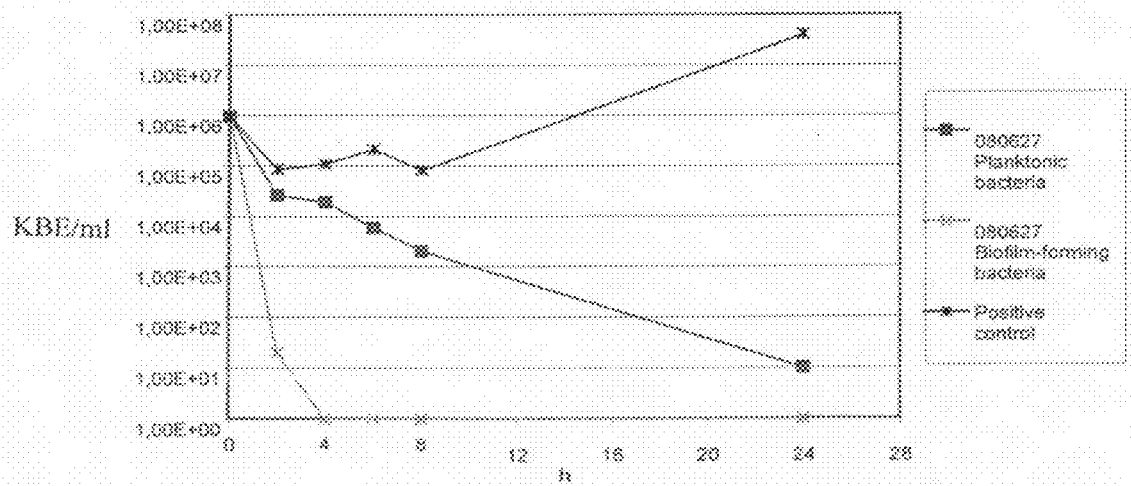
FIG. 2 is a plot of development of cell number of staphylococcus aureus ATCC 25923 after culture on a partially copper-coated TiAlV-surface versus time in hours.

Even after only 4 hours no living bacteria were found on the cylinders and after 24 hours only very few living bacteria were found in the buffer solution (FIG. 2).

The invention claimed is:

1. A coated implant comprising
a substrate having a surface; and
an anti-infective coating on the surface of the substrate;
wherein the substrate titanium;
wherein the anti-infective coating comprises a titanium oxide layer and particles of an anti-infective metal connected to the titanium oxide layer;
wherein the titanium oxide layer comprises a conversion layer and a porous titanium oxide layer on the conversion layer formed by anodic oxidation of the substrate surface in an alkaline electrolyte solution;

wherein the particles of the anti-infective metal are electro-deposited in the porous titanium oxide layer and the porous titanium oxide layer containing the anti-infective metal is solidified by blasting to form island-like anti-infective metal particles connected to said titanium oxide layer.

2. The coated implant of claim 1, wherein the anti-infective metal is selected from the group consisting of copper, silver, zinc and mixtures thereof.

3. A method for producing an anti-infective coating on an implant comprised of titanium according to claim 1, the method comprising the steps of anodically oxidizing a surface of the implant in an electrolyte comprising an alkaline solution to form a porous titanium oxide layer on the implant surface, wherein the pores of the titanium oxide layer having an electrical conductivity sufficient for electro-deposition of an anti-infective metal in the pores;

electro-depositing in the pores a metal having anti-infective properties to form a titanium oxide layer containing the anti-infective metal; and blasting the anti-infective metal-containing titanium oxide layer to form a solidified anti-infective metal-containing titanium oxide layer.

4. The method according to claim 3, wherein the electrolyte for said anodic oxidation comprises sodium hydroxide.

5. The method according to claim 3, wherein the electrolyte for said anodic oxidation comprises sodium silicate.

6. The method according to any one of claims 3 to 5, wherein the metal is selected from the group consisting of copper, silver, zinc and mixtures thereof.

7. The method according to claim 3, wherein the anti-infective metal containing titanium oxide layer has a thickness of from 8 to 15 µm.

8. The method according to claim 3, wherein the blasting step comprises blasting the anti-infective metal-containing titanium oxide layer with glass beads.

* * * * *